(12) United States Patent
Kaplan

(10) Patent No.: US 6,276,533 B1
(45) Date of Patent: Aug. 21, 2001

(54) WEIGHT-SPECIFIC ELIXIR DOSAGE CALCULATION REFERENCE

(76) Inventor: Brian Kaplan, 19060 SE. Kokomo La., Jupiter, FL (US) 33458

( * ) Notice: Subject to any disclaimer, the term of this patent is extended or adjusted under 35 U.S.C. 154(b) by 0 days.

(21) Appl. No.: 09/505,592

(22) Filed: Feb. 16, 2000

(51) Int. Cl.$^7$ .................................................. B65D 83/04
(52) U.S. Cl. ..................... 206/534; 206/459.1; 116/309; 215/228
(58) Field of Search .................................. 206/528, 534, 206/459.5, 459.1; 40/310; 215/228, 230; 283/65, 115; 116/309, 318

(56) References Cited

U.S. PATENT DOCUMENTS

| | | |
|---|---|---|
| 3,151,599 | 10/1964 | Livingston . |
| 3,355,067 | 11/1967 | Espinal . |
| 3,572,282 | 3/1971 | Tump et al. . |
| 3,960,713 | 6/1976 | Carey . |
| 4,041,628 | 8/1977 | Sasson . |
| 4,594,070 * | 6/1986 | Stoddard ............................... 116/309 |
| 4,666,051 | 5/1987 | Trick . |
| 4,749,093 | 6/1988 | Trick . |
| 4,753,189 | 6/1988 | Mastman et al. . |
| 4,920,912 | 5/1990 | Kirkling . |
| 5,009,338 * | 4/1991 | Barker .................................. 206/534 |
| 5,011,032 | 4/1991 | Rollman . |
| 5,188,251 * | 2/1993 | Kusz .................................... 206/534 |
| 5,279,422 | 1/1994 | Adams . |
| 5,358,117 | 10/1994 | Adams . |
| 5,377,614 | 1/1995 | Glazer . |
| 5,520,307 * | 5/1996 | Miller et al. ......................... 206/534 |
| 5,577,335 * | 11/1996 | Tucker ................................. 206/534 |
| 5,678,712 * | 10/1997 | Rios ..................................... 206/534 |

* cited by examiner

*Primary Examiner*—Luan K. Bui
(74) *Attorney, Agent, or Firm*—McHale & Slavin

(57) ABSTRACT

A calculation aid is disclosed forming an integral part of a medication bottle or closure cap. The calculation aid, in essence, is a detailed weight-dose conversion chart, promoting the accurate dispensing of the weight-specific dosage of a given elixir to a child. The closure cap or bottle includes a parallel rows of indicia for the weight a child, calculated doses appropriate for the specific weight, and calculated quantity of elixir corresponding to the calculated dose. An aperture sleeve allows selected viewing of the indicia.

7 Claims, 2 Drawing Sheets

WEIGHT-SPECIFIC ELIXIR DOSAGE CALCULATION REFERENCE

FIELD OF THE INVENTION

The present invention relates to improvements in medicine bottles and more specifically, to a weight-specific dosage calculation aid for elixirs to provide a reference source on a medicine bottle for calculating doses of an elixir based upon an individual's weight.

DESCRIPTION OF THE PRIOR ART

Currently, pediatric elixirs such as acetaminophen, ibuprofen and decongestants/cough suppressants are packaged in bottles which have vague and wide ranges of dosing recommendations for children of different weights. For instance, some dosing recommendations on bottles are based on the child's age. However, pediatric elixir dosing is specifically to be based on weight as per the Physician's Desk Reference. This is especially critical in view of the significant variations of weights of children of the same age making a dosage determination based on age, not only inaccurate, but most dangerous.

Without a direct reference, even elixirs prescribed by a physician can lead to inappropriately low doses of a medication. For instance, when a child's physician instructs a child's guardian to deliver a certain amount of elixir to a child on a certain date, should the guardian continue to give the child the same amount of medication months later, the dosage will not be correct if the child's weight has changed. A child's weight can change quickly and if the guardian does not inform the physician of the weight change, the dosage will be improper. Continual adjustments in dosing, necessitated by the child's rapidly changing body weight, is important to ensure maximum therapeutic response to a medication. As a physician, it is not uncommon to hear a parent inquire as to why their child's fever has not gone down despite the use of medication prescribed four months earlier. Or more critically, why does my child's fever increase shortly after receiving a dose of the acetaminophen.

Although there currently exist weight-specific dosage calculations presented on charts and pinwheels, they are not readily available to the general public. Even if available, the charts could present a confusing array of dosages that may not be understood by the general consumer. The Physician's Desk Reference may be used for the calculation but such a reference book is not typically purchased or understood by the average consumer.

The use of bottle mounted or integrated indicators are known in the art but have a primary purpose to act as: a) dosage schedule reminders; b) as a reminder as to whether the last dose was taken; or c) as a reminder of the number of pills to take at each dosage interval.

U.S. Pat. No. 4,666,051 discloses a bottle located memory aid for use in indicating one in a sequence of predetermined times for dispensing medication.

U.S. Pat. No. 4,749,093 discloses a memory aid for use in reminding patients to take medicine that can accommodate different dosage schedules for the medicine.

U.S. Pat. No. 5,377,614 discloses an indicator showing weekday, date and time for taking a pill or other medicinal dose.

U.S. Pat. Nos. 5,358,117 and 5,279,422 disclose bottle indicators having indicia circumferentially marked around the bottle representing the next time for taking medicine.

U.S. Pat. No. 4,920,912 discloses a time dial which indicates both when medication was last taken and when medication should be taken next.

U.S. Pat. No. 5,011,032 discloses a patient dosage regimen compliance cap which reminds a patient which dose was last take or which dose is yet to be taken and displays the number of medication units to take at each administration.

U.S. Pat. No. 4,753,189 discloses a medicine bottle cap having a dosage indicator to indicate the next dosage time or other information for the user. The indicator is moved incrementally from one location to another to indicate the time for the next dosage, following the removal of medicine from the bottle.

Other dosage indicating closures for medicine bottles have been known and used in the past including: U.S. Pat. Nos. 3,151,599; 3,355,067; 3,572,282; 3,960,713; 4,041,628;

While the prior art is directed to memory aids to remind patients 1) what days to take their prescribed medications, 2) the number of times per day to take the medications, 3) when they took their last dose, 4) when they are to take their next dose, 5) the number of pills to take at each dosing interval, no prior art exists for a calculation aid to determine the exact weight-specific dose of an elixir for a patient, of which children require the most specific determination due to their size and ever changing weight.

Thus, what is needed is an in-cap or bottle-mounted weight-specific dosage calculation reference provides a convenient, user-friendly, immediately accessible way to assure that a child requiring an elixir will attain its maximal therapeutic effects by receiving the exact dose recommended for the child, given the child's weight. Conversely, an integrated weight-dosage conversion reference will virtually eliminate the occurrence of children receiving inappropriately high dosages for their weight, mistakes which in some cases are potentially toxic or even lethal.

SUMMARY OF THE INVENTION

This invention is a weight-specific dosage calculation reference for use with elixirs. The calculation reference employs narrow apertures on a rotating collar allowing a plethora of specific dosing recommendations inscribed on a bottle cap or on the side of a bottle.

In a preferred embodiment of the invention, provided is an in-cap reference for a specific elixir's previously calculated doses corresponding to specific pediatric patient weights. In an alternative embodiment, provided is a bottle mounted reference for a specific elixir's previously calculated doses corresponding to specific pediatric patient weights.

Thus an objective of the invention is to provide accurate, calculated information as an integral part of the elixir bottle's cap or bottle.

Another objective of the invention is to eliminate the need for reference books, pinwheels, or the like disjointed materials that are used for calculation but do not form an integral portion of the bottle.

Another objective of the invention is to provide a format available to both the physician and average consumer for providing specific elixir dosages that are dependent on the weight of the child.

Still another objective of the invention is to provide a specific dosage calculator that has application for adults, children, and pets.

Another objective of the invention is to reduce the exposure of an inappropriately high dose of medication due to vague and wide ranges currently provided on most elixir bottles designed to address the average child's weight at a particular age.

Another objective of the invention is to promote achieving the best therapeutic outcome by helping avoid inaccurate dosing.

Yet still another objective of the invention is to provide a device that allows for calculating the proper dose of medication as the dosage pertains to the weight of an adult, child or pet.

It is a further objective of this invention to maximize the therapeutic effects of a medication by promoting accurate dosing.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Figure 1:
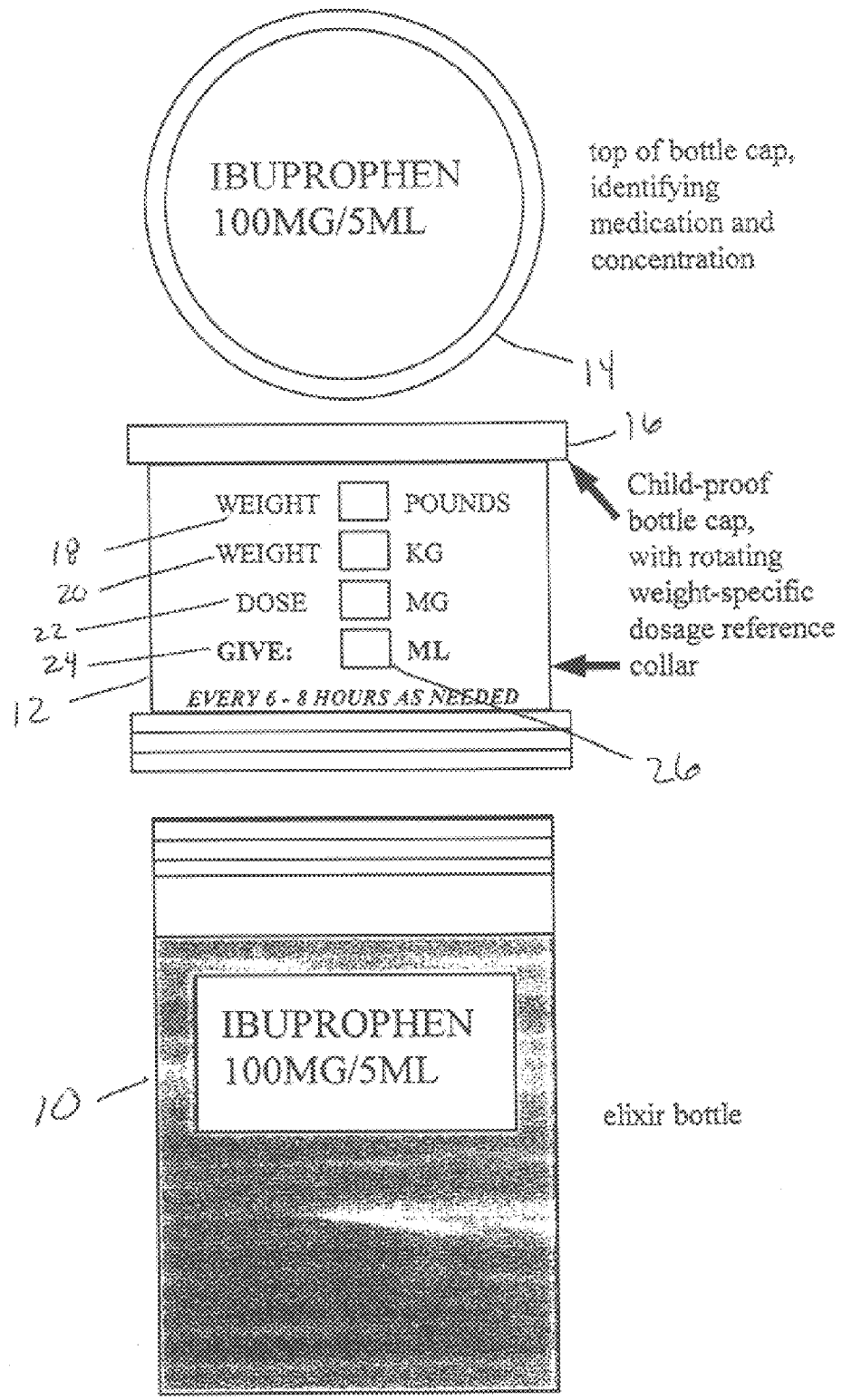
FIG. 1 shows an exploded perspective view of the calculation aid of this invention.

Now referring to FIG. 1, set forth is the preferred embodiment of the instant invention in which a calculation aid is used with medication bottle 10 having an open top and a closure or bottle cap 12 which includes a calculation reference chart formed integral to the cap 12. In the most basic form, the cap 12 is made from two components, an inner component 14 used for locking and an outer component 16 or sleeve having an aperture for viewing of the calculation reference. Preferably the closure cap is tamper-proof.

The inner component 14 functions to provide the traditional child-proof closure for the medication bottle and includes inscribed indicia set forth in four parallel rows. One row contains various children weights in pounds 18, a second row containing a child's weight in kilograms 20, a third row providing the previously calculated dose appropriate for that specific weight in milligrams 22, and a fourth row to provide the quantity of elixir in milliliters corresponding to that dose 24. The outer member 16 is a freely rotating plastic collar which has one column 26 of four apertures providing distinct windows for each of the above mentioned rows. The top aperture is inscribed: "WEIGHT in POUNDS"; the next aperture is inscribed: "WEIGHT in KG"; the next aperture is inscribed: "DOSE in MG"; and the bottom aperture is inscribed: "GIVE: ML". The calculation aid, as it is weight specific and not patient specific, can be mass distributed on over-the-counter medications as opposed to requiring a pharmacist to set and permanently fix or secure it to denote a specific patient's needs.

The calculation reference functions by the rotation of the plastic collar 16. An individual advances the collar to display the child's weight in the first or second apertures 26. In turn, the dose in milligrams and quantity in milliliters are displayed in the third and fourth apertures.

Figure 2:
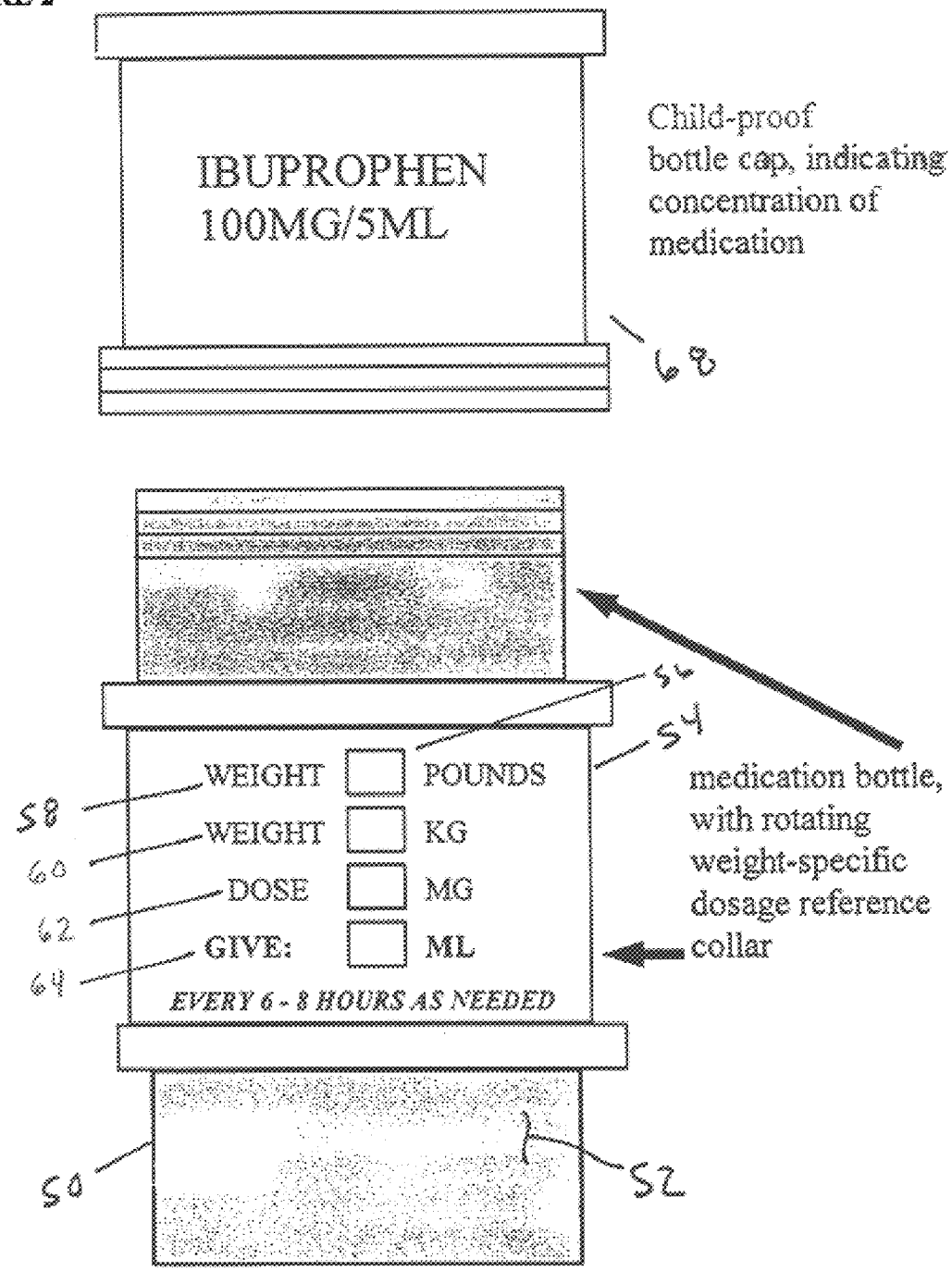
FIG. 2 shows an exploded view of another embodiment of the calculation aid of this invention.

Referring to FIG. 2, set forth is another embodiment of the current invention wherein the calculation reference is part of the medication bottle. In this embodiment, a medication bottle 50 includes a calculation reference chart formed integral to the medication bottle surface 52. An outer sleeve 54 is slidable along the outer surface of the bottle and includes an aperture row 56 for viewing of the calculation reference.

The aperture row is for viewing of the inscribed indicia set forth in four parallel rows. One row contains various children weights in pounds 58, a second row containing a child's weight in kilograms 60, a third row providing the previously calculated dose appropriate for that specific weight in milligrams 62, and a fourth row to provide the quantity of elixir in milliliters corresponding to that dose 64.

The outer member 54 is a freely rotating plastic collar which has one column 56 of four apertures providing distinct windows for each of the above mentioned rows. The top aperture is inscribed: "WEIGHT in POUNDS"; the next aperture is inscribed: "WEIGHT in KG"; the next aperture is inscribed: "DOSE in MG"; and the bottom aperture is inscribed: "GIVE: ML". A cap 68 is used for containment of the medication and may be of any child proof design. The calculation reference functions by the rotation of the plastic collar 54.

An individual advances the collar to display the child's weight in the first or second apertures 56. The dose in milligrams and quantity in milliliters are displayed in the third and fourth apertures.

The calculation aid employs indicia directed to a specific medication of a specific concentration. This strict condition comes with the understanding that different weight dose conversion factors are required: a) when the same medication is manufactured at a different concentration, b) when relating to different medications altogether. As a general precaution, the medication name and concentration is to be inscribed upon the top of the cap, so that its user can verify that the inscribed calculations do, in fact, relate to the medication within the bottle to which it is attached.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What I claim is:

1. A calculation aid for a medicine bottle, said calculation aid comprising: a bottle having an open top, a closure cap for sealing of said open top, and a calculating means for determining an elixir dosing output based upon a weight input, said calculating means formed integral to said closure cap wherein said closure cap includes at least one row of indicia for weight, one row of indicia for calculated doses appropriate for a specific weight, and one row of indicia for calculated quantity of elixir corresponding to said calculated dose, and an aperture sleeve allowing selected viewing of said indicia.

2. The calculation aid according to claim 1 wherein said aperture sleeve is rotatably secured to said closure cap.

3. The calculation aid according to claim 1 wherein said closure cap is tamper-proof.

4. The calculation aid according to claim 1 including a row of indicia for weight displayed in lbs or kg.

5. A calculation aid for a medicine bottle, said calculation aid comprising: a bottle having an open top, a closure cap for sealing of said open top, and a calculating means for determining an elixir dosing output based upon a weight input, said calculating means formed integral to said bottle wherein said bottle includes at least one row of indicia for weight, one row of indicia for calculated doses appropriate for a specific weight, and one row of indicia for calculated quantity of elixir corresponding to said calculated dose, and an aperture sleeve allowing selected viewing of said indicia.

6. The calculation aid according to claim 5 wherein said aperture sleeve is rotatably secured to said bottle.

7. The calculation aid according to claim 5 including a row of indicia for weight displayed in lbs or kg.

* * * * *